United States Patent [19]

Thorpe et al.

[11] Patent Number: 5,162,229

[45] Date of Patent: * Nov. 10, 1992

[54] DEVICE AND METHOD FOR ENHANCED RECOVERY AND DETECTION OF MICROBIAL GROWTH IN THE PRESENCE OF ANTIMICROBIAL SUBSTANCES

[75] Inventors: Thurman C. Thorpe; James L. DiGuiseppi, both of Durham; Richard C. Driscoll, Raleigh, all of N.C.; James E. Turner, Hillsboro, Oreg.; Michael J. Calandra, Somerset, N.J.

[73] Assignee: Akzo N.V., Arnhem, Netherlands

[*] Notice: The portion of the term of this patent subsequent to Jul. 31, 2007 has been disclaimed.

[21] Appl. No.: 732,569

[22] Filed: Jul. 19, 1991

Related U.S. Application Data

[63] Continuation-in-part of Ser. No. 480,398, Feb. 15, 1990, Pat. No. 5,094,955, which is a continuation-in-part of Ser. No. 322,874, Apr. 13, 1989, which is a continuation-in-part of Ser. No. 168,291, Mar. 15, 1988, Pat. No. 4,945,000.

[51] Int. Cl.$^5$ .............................................. C12M 1/34
[52] U.S. Cl. ..................... 435/291; 435/34; 435/287; 435/313; 435/807; 436/146
[58] Field of Search ............... 435/291, 289, 288, 287, 435/284, 286, 296, 34, 29, 313, 807, 808; 436/146; 422/68, 52

[56] References Cited

U.S. PATENT DOCUMENTS

| Re. 31,879 | 5/1985 | Lübbers et al. ............... 436/133 |
| 2,880,070 | 3/1959 | Gilbert . |
| 3,067,015 | 12/1962 | Lawdermilt . |
| 3,676,679 | 7/1972 | Waters .................... 250/83.6 FT |
| 3,853,712 | 12/1974 | House et al. ............... 195/127 |
| 3,998,591 | 12/1976 | Eckfeldt .................. 23/253 R |
| 4,004,981 | 1/1977 | Hurni et al. .............. 195/127 |
| 4,073,691 | 2/1978 | Ahnell et al. ............ 195/103.5 M |
| 4,101,383 | 7/1978 | Wyatt et al. ............ 195/103.5 M |

(List continued on next page.)

FOREIGN PATENT DOCUMENTS

| 472420 | 2/1973 | Australia . |
| 0104463 | 4/1984 | European Pat. Off. . |
| 0118274 | 9/1984 | European Pat. Off. . |
| 0255087 | 2/1988 | European Pat. Off. . |
| 0301699 | 2/1989 | European Pat. Off. . |
| 0333253 | 9/1989 | European Pat. Off. . |
| 57-207861 | 12/1982 | Japan . |
| 8100304 | 2/1981 | World Int. Prop. O. . |

OTHER PUBLICATIONS

"Optical Sensors for pH and Blood Gas Analysis," Marsoner et al., IFCC Workshop, Helsinki, 1985.
"Simplex Optimization of a Fiber-Optic Ammonia Sensor Based on Multiple Indicators," Rhines et al., 60 Anal. Chem. 76-81 (1988).
"Fiber-Optic Fluorescing Sensor for Ammonia," Wolfbeiss et al., 185 Analytica Chemica ACTA, 321-327 (1986).
McFaddin, Biochemical Tests for Identification of Medical Bacteria, pp. 187-193 and 108-117 (1976).

Primary Examiner—Robert J. Warden
Assistant Examiner—Krisanne M. Thornton
Attorney, Agent, or Firm—Donna Bobrowicz; William M. Blackstone

[57] ABSTRACT

The present invention relates to a device and method of detecting microorganisms in a rapid manner and increasing the number of microorganisms detected during the culturing of a sample by the addition of resinous and non-resin adsorbents and molecular sieves in the growth media. These agents have been found to neutralize or remove inhibitory and antimicrobial substances found in samples and media.

14 Claims, 1 Drawing Sheet

U.S. PATENT DOCUMENTS

| | | | |
|---|---|---|---|
| 4,145,304 | 3/1979 | Melnick et al. | |
| 4,152,213 | 5/1979 | Ahnell | 195/103.5 M |
| 4,182,656 | 1/1980 | Ahnell et al. | 435/34 |
| 4,236,211 | 11/1990 | Arvesen | 364/413 |
| 4,238,334 | 12/1980 | Halbfoster | |
| 4,283,492 | 8/1981 | Imanaka et al. | 435/47 |
| 4,289,248 | 9/1981 | Lynn | 215/330 |
| 4,306,877 | 12/1981 | Lübbers | 23/230 R |
| 4,330,622 | 5/1982 | Desai | 435/34 |
| 4,407,959 | 10/1983 | Tsuji et al. | 435/288 |
| 4,456,380 | 6/1984 | Kondo et al. | 356/418 |
| 4,557,900 | 12/1985 | Heitzmann | 422/55 |
| 4,568,518 | 2/1986 | Wolfbeis et al. | 422/56 |
| 4,632,902 | 12/1986 | Waters et al. | |
| 4,672,039 | 6/1987 | Lundblom | 435/291 |
| 4,698,308 | 10/1987 | Ikeda | 435/291 |
| 4,780,191 | 10/1988 | Romette et al. | 204/403 |
| 4,784,947 | 11/1988 | Noeller | 435/33 |
| 4,889,992 | 12/1989 | Hoberman | 250/343 |
| 4,945,060 | 7/1990 | Turner et al. | 435/291 |
| 4,971,900 | 11/1990 | Ahnell et al. | 435/29 |
| 5,047,331 | 9/1991 | Swaine et al. | 435/29 |
| 5,094,955 | 3/1992 | Calandra et al. | 435/291 |

DEVICE AND METHOD FOR ENHANCED RECOVERY AND DETECTION OF MICROBIAL GROWTH IN THE PRESENCE OF ANTIMICROBIAL SUBSTANCES

BACKGROUND OF THE INVENTION

This application is a continuation-in-part of application Ser. No. 480,398, filed Feb. 15, 1990, now U.S. Pat. No. 5,094,955 which is a continuation-in-part of application Ser. No. 322,874, filed Apr. 13, 1989, which is a continuation-in-part of application Ser. No. 168,291, filed Mar. 15, 1988, now U.S. Pat. No. 4,945,060, all of which are herein incorporated by reference.

The present invention relates to a device and method of detecting microorganisms in a rapid manner and increasing the number of microorganisms detected during the culturing of a sample by the addition of resinous and non-resin adsorbents and molecular sieves in the growth media. These agents have been found to neutralize or remove inhibitory and antimicrobial substances found in samples and media.

It is standard practice to detect the presence of microorganisms in samples by culturing samples in a liquid growth medium. Medical test samples include body fluids such as blood, urine and cerebral spinal fluid and other solid or semi-solid samples such as tissue fluidized in saline or other liquid reagents. Industrial samples include pharmaceuticals, foods or any product that must be tested for the presence or levels of microorganisms.

The detection of these microorganisms can be impaired by the condition of the samples themselves. For example, medical samples may contain levels of antibiotics due to treatment regimens, while it is known that serum, plasma and lysed erythrocytes naturally contain microbial inhibitors. Industrial samples such as pharmaceuticals and foods may also contain antimicrobials or preservatives that inhibit the growth of microorganisms. Additionally, when culture media is prepared, autoclaving of the media at very high temperatures under pressure can result in the formation of by-products toxic to microorganisms. Removal or neutralization of these inhibitory or bactericidal substances is necessary to detect microbial contamination.

The use of synthetic anionic exchange and nonionic adsorbent resins for removal of antimicrobial substances is well known and has been previously described for use in medical diagnostic procedures. In particular, these resins have been shown useful in the removal of antibiotics and other antimicrobials from blood samples. The removal of these inhibitors in medical samples allows for recovery and faster detection of microorganisms so that microbial identification and accurate antibiotic susceptibility testing can be performed.

Melnick et al., U.S. Pat. No. 4,145,304, describes the use of synthetic anionic exchange and nonionic resins to remove antimicrobials, including antibiotics, from body fluids, thus allowing for recovery of pathogens using standard culture techniques. The resins described are coated with a nonionic detergent in order to selectively remove charged antibiotics while inhibiting adherence of bacteria to the resins. After treatment of the sample with the resin, the eluate is cultured in a growth media. The degree of binding of antibiotics by the resins is indicated to be dependent on the total exchange capacity, pore diameter, and surface area of the resin.

Waters, U.S. Pat. No. 4,632,902, herein incorporated by reference, describes an improvement over Melnick by incorporating ion exchange resins and non-functional adsorbent resins directly into the growth medium. Inhibitors removed include antibiotics administered to patients and naturally occurring inhibitors contained in serum, plasma, and lysed erythrocytes. The resins are not coated with a nonionic detergent or surfactant before use and the pore size of the resin is not critical.

The use of resins as described above indicates that detergent treatment of the resins, in particular, the nonionic polystyrene resin which is extremely hydrophobic, may or may not be necessary. The confusion may be due to the fact that nonionic polystyrene resins are generally pretreated with surfactants by the manufacturer prior to shipment in order to be used in hydrophilic environments. Therefore, treatment with surfactants or detergents is an absolute requirement to wet these resins, thus allowing for hydrophilic interaction, particularly with broth culture medium. If the hydrophobic resin is not treated, the resin will float at the top of a liquid culture medium without any interaction possible to bind antimicrobial components.

However, using adsorbents in culture media can cause nonspecific binding of proteins, carbohydrates and other media components to the adsorbent. If enough of these components are bound and therefore not accessable to the microorganisms, no microorganisms will be detected. This binding is dependent on the ratio of the adsorbent to media volume and concentration.

The removal of toxic by-products as well as growth components from medium influences its color. Depending on the amount of adsorbent material and the composition of the particular medium, it may become colorless, which may indicate an inability to support growth. However, the ability of the medium to support growth is not always indicated by color, as chemically defined or semi-defined media are colorless and can still maintain optimal growth performance.

The culture medium formulation is critical in providing optimized growth for a wide variety of microorganisms. This is particularly important when the production of carbon dioxide is used as the measure of microbial growth, for example, as described in U.S. Pat. No. 4,945,060. The proper ratio of growth promoting components is essential to provide optimal carbon dioxide production from a variety of microorganisms with diverse metabolic pathways in order to rapidly detect microbial growth. The removal of medium components by any adsorbent material must be carefully controlled to maintain the optimal carbon dioxide production required for detection of microorganisms, especially if no additional growth supplements, such as blood, are added.

The use of synthetic resins in culture medium improves recovery of microorganisms from body fluids, and especially from blood. These fluids are nutritious and therefore compensate for a lack of nutrients in the adsorbent containing culture medium. However, in situations where the test sample can add no nutritional value to the medium containing the resins, the ability to recover and detect microorganisms can be greatly compromised.

When antimicrobials are removed from or neutralized in culture medium, the degree of neutralization is dependent on a number of factors. These factors include the dilution ratio of the sample to the medium, the concentration of the antimicrobial in the sample, and the antimicrobial sensitivity of the particular organism contained in the sample. In the case of blood samples from patients on antibiotics, there is a maximum therapeutic level of a particular antibiotic that can be achieved that differs with each antibiotic. Therefore, in an optimal testing situation, the amount of adsorbant should vary with each sample.

Although synthetic resins are known to remove inhibitory substances in cultures containing body fluids, it is desirable to find other substances that perform a similar function on both body fluids and non-body fluid samples, such as foods and industrial products. The present invention removes, inhibits, or isolates antimicrobials in test samples, while retaining the components of the medium necessary to recover and detect microorganisms in a rapid manner.

SUMMARY OF THE INVENTION

The invention is a device and a method for the enhanced recovery and detection of microorganisms in samples cultured in a growth medium containing adsorbents that are resins or non-resinous adsorbants in the presence of antimicrobial substances. The neutralization, binding, or inhibition of antimicrobial substances is not limited to those found in body fluids, but also includes industrial samples containing inhibitory substances and toxic by-products inherently contained in microbial growth media.

The device for the enhanced recovery and detection of microorganisms and for continuously monitoring biological activity in a sample comprises a sealable specimen container, having an internal chamber in which a sample may be cultured with a sterile culture medium and adsorbents that are resins or non-resinous adsorbents or combinations thereof, in amounts that are effective in neutralizing, binding, or inhibiting antimicrobial substances present in said sample and said medium, having at least one transparent section in said container and a sensor means located inside said container in the region of the transparent section, whereby changes in the appearance of the sensor means can be continuously monitored from the exterior of the container through the transparent section, thereby monitoring biological activity without violating the integrity of the container after sealing. The sensor means comprises a membrane, which is an attachment or support medium, and an indicator medium, the indicator medium being selected for its ability to exhibit a detectable change when exposed to products of an organism's metabolic activity.

The method for enhanced recovery and detection of microorganisms in culture comprises preparing culture medium, adding to the medium non-resinous adsorbents in amounts that are effective in neutralizing, binding or inhibiting antimicrobial substances to the culture medium, inoculating the medium with a sample, incubating and determining the results.

Figure 1:
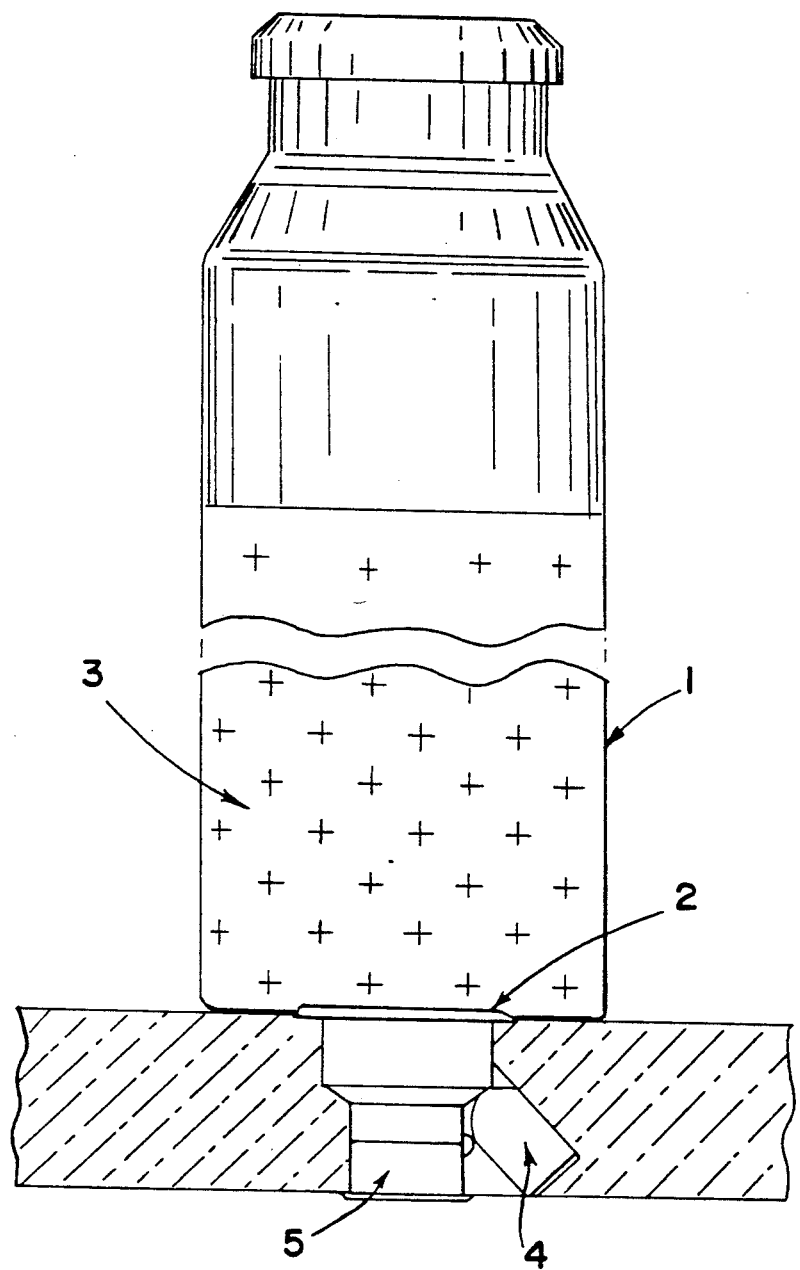
FIG. 1—Blood culture instrument.

This drawing shows the overall appearance of the device and the functional part of an instrument that may be used to monitor the device. Illustrated are (1) the container, (2) the sensor, (3) the culture medium containing a resinous or non-resinous adsorbent, (4) the light source, and (5) the photodetector.

In operation, the entire device is placed on an agitator inside an incubator, which provides a suitable environment for microbial growth and excludes room light from the photodetectors.

DETAILED DESCRIPTION OF THE INVENTION

One embodiment of the instant invention is a device for detecting of microbial growth by classical methods of visual inspection for turbidity or by detecting the growth of microorganisms by their production of metabolites, for example, by detecting carbon dioxide through the use of a carbon dioxide sensor bonded internally to the device, as described in co-pending U.S. Ser. No. 322,874 and U.S. Pat. No. 4,945,060. This device can also include materials in the culture medium such as the resinous materials described in U.S. Pat. No. 4,632,902, and non-resinous adsorbent materials that neutralize, bind, or inhibit antimicrobial substances from samples in the culture media, and which therefore allow for greater recovery and detection of microorganisms in these samples.

Generally, antimicrobial substances include, among others, antibiotics, antibiotics in body fluid samples, preservatives, bacteriostats, bactericides, and any toxic by-products produced during the preparation of culture media. Antimicrobial substances also include naturally occurring components in blood such as complement and antibodies.

The term "adsorbents" for the purposes of this application, includes all adsorbent materials that neutralize, bind, and inhibit antimicrobial substances. These adsorbents include resins as defined in U.S. Pat. No. 4,632,902, and non-resinous adsorbents.

As used herein, "resin" is a subclass of adsorbents, and is further defined to include naturally occurring and synthetic resins, for example ion exchange resins, nonfunctional polymeric resin adsorbents and, in particular, polystyrene resins cross-linked with divinyl benzene.

The preferred materials, "non-resinous adsorbants" as used herein, are another subclass of adsorbents and are defined as naturally occurring and synthetic non-resin adsorbents and molecular sieves that can be used for clarifying, deodorizing, decolorizing, and filtering. Some of these non-resinous adsorbents are the same as those used during the production of antibiotics to remove antibiotics from culture medium growing antibiotic-producing bacteria. Whether or not these bacteria are injured during the process is unknown, as is the degree of recoverability of these bacteria remaining in the medium.

These non-resinous adsorbents include various forms of 1) aluminum oxide (alumina), 2) colloidal native hydrated aluminum silicates (clays), such as bentonite, kaolin, and fuller's earth, 3) crystalline hydrated alkali-aluminum silicates (sodium or calcium zeolites), 4) silica (silica gel, silica beads) such as Davisil, 5) siliceous frustules and fragments of various species of diatoms (infusorial earth, diatomaceous earth) such as Celite TM (Manville Products Corporation, Denver, Colo., USA) and 6) amorphous carbon (in particular, activated carbon) such as Carboraffin, Norit TM (American Norit Company Inc., Jacksonville, Fla., USA), Opocerbyl, and Ultracarbon. Naturally occurring adsorbent activated charcoal, which has been used to prevent the lethal effects of oxidation in transport media and growth media, can also be used. This media has been used for the transport of fastidious organisms such as Neisseria gonorrhoeae and the cultivation of Legionella species. Non-resinous adsorbents do not require pre-treatment with a surfactant in order to function. Treatment with surfactants may even decrease the adsorbtive capabilities of these materials.

The use of adsorbents at an appropriate ratio to medium can also remove toxic by-products produced in autoclaved media and still provide an optimal nutritious culture medium while maintaining the ability to neutralize antimicrobial substances.

Many of these non-resinous adsorbents remove antimicrobial substances in culture. Preferred non-resinous adsorbents are the colloidal native hydrated aluminum silicates (clay) and the amorphous carbon (activated carbon) groups of adsorbent materials. Additionally preferred materials are fuller's earth or activated charcoal used singularly or in combination.

Particularly preferred non-resinous adsorbents are high activity activated charcoal bound to celluose fibers (Ecosorb® GL 241), fuller's earth bound to cellulose fibers (Ecosorb® GL 247) and high activity activated charcoal bound to fuller's earth (Ecosorb® GL 248). These materials are produced by Graver Chemical, Union, N.J., USA, primarily using the Ecosorb® process as described in U.S. Pat. No. 4,238,334, and incorporated by reference herein. In short, filter aid materials, which are generally fibers such as cellulose, nylon fibers, rayon fibers, polypropylene fibers and polyvinyl chloride fibers, and can be either negatively or positively charged, are treated with an electrolyte-type compound that produces a surface charge opposite to its normal surface charge. The treated filter aid material is mixed, in an aqueous suspension, with an active particulate material that has an opposite charge from the filter aid material, to produce the final adsorbant or filter material.

Compounds that can be used to produce a reversed surface charge on the fibers must have a plurality of charge sites so that a bond may be formed with the filter aid material and excess charge sites also remain to produce a surface charge which is the reverse of the normal surface charge. Examples of suitable cationic organic polyelectrolytes include polyalkylene imines, polyalkylene polyamines, and polyvinylbenzyl quaternary amonium salts.

The device contains culture media formulated to be useful with the present adsorbents. These include most general purpose media such as tryptic soy broth, brain heart infusion broth, Columbia broth, and Brucella broth. Quantities of non-resinous adsorbents resulting in neutralization of antimicrobial substances are added to the culture media, and range from about 0.025 to about 0.50 grams per milliliter of medium, depending on the culture medium.

Enhancement of growth performance in the presence of non-resinous adsorbents due to detoxification of the medium is species dependent. This is due to the differences in sensitivities of the test organism to toxic by-products inherently present in the medium. As shown in Table 2, in Example 2, $E.\ coli$ and $X.\ maltophilia$ had identical detection times in media that had no adsorbents and in media that contained charcoal bound to fuller's earth, while $P.\ aeruginosa$ took longer to detect with the adsorbent. $H.\ influenzae$, $N.\ meningitidis$, $S.\ aureus$, $S.\ pneumoniae$ and $S.\ pyogenes$ all were detected in less time with the non-resinous adsorbent than without it.

The medium formulation can be, if required, of a composition that allows for recovery and detection of contaminating organisms from industrial samples, such as pharmaceuticals, that have no additional nutritional value. Furthermore, the interaction of the adsorbent material with the medium can be manipulated, if necessary, to eliminate toxic byproducts in the medium, allowing for enhanced recovery and detection of microorgansims independent of the addition of a sample. In order to do this, one skilled in the art would balance the amount of adsorbent with the amount of medium and test the final composition for its neutralizing capability and the growth performance of test organisms, in the presence and absence of antimicrobials.

The sample is introduced into the device, and the device is incubated until either positive growth is detected or, generally, until 5-7 days have passed and no growth is detected.

The present adsorbants are not limited to use in the device. They may be added to any standard culture media, which is then inoculated with a sample, incubated at the correct temperature for an appropriate time for the type of sample being tested, while usually shaken or rocked in order to expose more surface area of the adsorbent to the liquid, to better contact any organisms present with nutrients and to avoid areas of high concentration of metabolic by-products. The temperatures and time periods needed for the determination of microorganism growth are well known to those skilled in the art and vary somewhat among different types of organisms.

The following examples are given to further illustrate features of the invention, but are not intended to limit the scope of the invention in any way.

EXAMPLE 1

Antibiotic Neuralization by Adsorbents

The culture bottle device used for the enhanced recovery and detection of microorganisms and for continuously monitoring biological activity in a sample is a sealable, sterilizable container with an internal chamber, which has at least one transparent section and a sensor means located inside the container in the region of the transparent section. The sensor changes appearance depending on the biological activity inside the container, and the changes can be monitored through the transparent section without violating the integrity of the container after sealing. The sensor is a solid support, such as a membrane, either intact or ground up or shredded, to which an indicator is bound or attached, and the indicator is selected for its ability to exhibit a detectable change when exposed to products of an organism's metabolic activity. The container, also known as the culture bottle, contains culture medium and an adsorbent, as described below, into which the sample is inoculated.

Culture bottles were made using a supplemented brain heart infusion broth to which the following non-resinous adsorbents were added: fuller's earth at a concentration of 0.13 g/ml; high activity activated charcoal bound to cellulose fibers at concentrations of 0.13 g/ml and 0.27 g/ml (Ecosorb GL 241); high activity activated charcoal bound to fuller's earth at concentrations of 0.09 g/ml and 0.17 g/ml (Ecosorb GL 248); and a mixture of Ecosorb GL 241 and Ecosorb GL 248 in a 1:1 ratio, at 0.13 g/ml. These bottles were then inoculated to achieve an initial inoculum of 10 to 100

CFU/ml of Staphylococcus aureus, ATCC 12600 (American Type Culture Collection, Rockville, Md., USA). The bottles were also inoculated with representative antibiotics, i.e., amikacin, cephalothin, clindamycin, erythromycin, gentamycin, methicillin, tetracycline and tobramycin, to achieve levels above the minimal inhibitory concentrations of those antibiotics for this strain of S. aureus. These antibiotic concentrations also represent the achievable therapeutic levels for humans following dilution of a blood sample in the culture media. A control containing no adsorbent was used. The inoculated bottles were then placed into the BacT/Alert TM Microbial Detection System (Organon Teknika Corporation, Durham, N.C., USA) for incubation and monitoring, with results being given automatically when the cultures became positive for microbial growth.

The results are given in Table 1. The last column shows that there was no growth of the test organism in the presence of antibiotics without non-resinous adsorbents in the culture medium. However, depending on the non-resinous adsorbent and its concentration, there is recovery and detection of the test organism with all of the antibiotics. Over this range of antibiotics, activated charcoal bound to cellulose fibers, and activated charcoal bound to fuller's earth at a concentration of 0.09 g/ml and 0.17 g/ml gave the best recoveries of S. aureus in all the various antibiotics. The time to detection with positive cultures was also dependent on the non-resinous adsorbent and its concentration.

pyogenes, and X. maltophilia. The initial inoculum ranged from 10 to 100 CFU/ml. No additional supplements were added to the medium except for the medium used to recover H. influenzae, where the growth factors found in horse blood were added. The inoculated bottles were then placed into the BacT/Alert TM Microbial Detection System for monitoring. Times to detection of positives are given in hours.

The data in Table 2 shows a significant decrease in the time to detection for several test organisms inoculated into medium containing the non-resinous adsorbent as compared to medium without it. The time to detection is species dependent, as shown in this table. H. influenzae, N. meningitidis, S. aureus, S. pneumoniae and S. pyogenes showed decreased time to detection in the presence of the adsorbent, whereas E. coli, P. aeruginosa and X. maltophilia showed no significant difference in time to detection with or without the adsorbent. This indicates that the non-resinous adsorbent is functional in removing the toxic by-products in the medium itself.

TABLE 2

Growth Performance of Microorganisms in the Presence of Adsorbents[1]
Time to Detection (Hours)[2]

| Microorganism | No Adsorbent | C + F[3] (0.09 g/ml) |
|---|---|---|
| Escherichia coli ATCC 25922 | 9.2 | 9.2 |
| Haemophilus influenzae[4] ATCC 35056 | 40.0 | 15.0 |
| Neisseria meningitidis ATCC 13090 | 28.8 | 18.7 |
| Pseudomonas aeruginosa ATCC 27853 | 12.7 | 13.2 |
| Staphylococcus aureus ATCC 25923 | 25.0 | 15.8 |
| Streptococcus pneumoniae ATCC 6305 | 50.4 | 12.2 |
| Streptococcus pyogenes ATCC 19615 | 21.0 | 14.3 |
| Xanthomonas maltophilia | 17.2 | 17.2 |

TABLE 1

Antibiotic Neutralization by Adsorbents with Staphylococcus aureus ATCC 12600[1]
Time to Detection (Hours)[2]

| Antibiotic (concentration) | FE[3] (0.13 g/ml) | C[4] (0.13 g/ml) | C (0.27 g/ml) | F-C[8] (0.13 g/ml) | C + FE[5] (0.09 g/ml) | C + FE (0.17 g/ml) | NO ADSORBENT |
|---|---|---|---|---|---|---|---|
| None | 11.2 | 11.3 | 11.5 | 11.0 | 10.8 | 10.9 | 10.9 |
| Amikacin (11.4 ug/ml)[6] | 11.5 | NG | 12.5 | 9.3 | 22.8 | 11.2 | NG[7] |
| Cephalothin (7.1 ug/ml) | NG | NG | 15.7 | NG | 88.8 | 19.8 | NG |
| Clindamycin (7.1 ug/ml) | NG | NG | 13.5 | 20.0 | 38.2 | 16.5 | NG |
| Erythromycin (7.1 ug/ml) | NG | 40.8 | 12.3 | 14.5 | 52.8 | 14.2 | NG |
| Gentamycin (4.0 ug/ml) | 12.0 | NG | 12.0 | 10.7 | 11.5 | 11.0 | NG |
| Methicillin (3.6 ug/ml) | NG | NG | 12.2 | 14.7 | 27.0 | 11.8 | NG |
| Tetracycline (7.1 ug/ml) | 16.5 | 24.2 | 12.5 | 11.2 | 12.5 | 11.7 | NG |
| Tobramycin (4.0 ug/ml) | 11.8 | 28.7 | 11.7 | 10.3 | 11.5 | 11.0 | NG |

[1]Initial inoculum was approximately 10 to 100 cfu/ml.
[2]Time to detection in hours was given automatically by the BacT/Alert Microbial Detection System.
[3]FE = Fuller's Earth
[4]C = high activity activitated charcoal bound to cellulose fibers.
[5]C + FE = high activity activated charcoal bound to Fuller's Earth.
[6]The concentration of antibiotics used were above the minimal inhibitory concentrations of S. aureus ATCC 12600 and are also in the therapeutically achievable range.
[7]NG = No Growth
[8]Fullers Earth bound to cellulose fibers + high activity activated charcoal bound to cellulose fibers at a 1:1 ratio

EXAMPLE 2

Growth Performance of Microorganisms in the Presence of an Adsorbent

Culture bottles as described in Example 1 were made with a supplemented brain heart infusion containing 0.09 g/ml of high activity charcoal bound to fuller's earth. Each bottle was then inoculated with one of the following microorganisms: E. coli, H. influenzae, N. meningitidis, P. aeruginosa, S. aureus, S. pneumoniae, S.

TABLE 2-continued

Growth Performance of Microorganisms in the Presence of Adsorbents[1]
Time to Detection (Hours)[2]

| Microorganism | No Adsorbent | C + F[3] (0.09 g/ml) |
|---|---|---|
| ATCC 13637 | | |

[1]Initial innoculum was approximately 10 to 100 cfu/ml.
[2]Time to detection was given automatically by the BacT/Alert Microbial Detection System.
[3]C + FE = high activity charcoal bound to Fuller's Earth.
[4]Horse blood was added for additional growth factors required for recovery of this organism.

EXAMPLE 3

Effect of Detergent Treatment on Antibiotic Neutralization of an Adsorbent

The procedures for preparing culture bottles, inoculum preparation, and antibiotic dilutions were the same as in Example 1. However, a sample of high activity activated charcoal bound to cellulose fibers was treated with an aqueous solution of 0.1% by weight of the surfactant Triton ™ X-100 (Rohm & Haas Co., Philadelphia, Pa., USA) and then washed thoroughly with water to remove residual surfactant. Culture bottles were then made with the same concentration of treated and untreated non-resinous adsorbent.

The results shown in Table 3 indicate that the treatment of the non-resinous adsorbent resulted in a decrease in the neutralization of certain antibiotics, and therefore the ability to recover microorganisms was reduced, with an increase in time to detection of the test organism in the presence of certain antibiotics.

TABLE 3

Effect of Detergent Treatment on Antibiotic Neutralization by an Adsorbent with *Staphylococcus aureus* ATCC 12600[1]
Time to Detection (Hours)[2]

| Antiobiotic (concen.) | No Adsorbent | C[3] (0.27 g/ml) | Detergent Treated[4] (0.27 g/ml) |
|---|---|---|---|
| None | 10.9 | 11.5 | 11.5 |
| Amikacin (11.4 ug/ml)[5] | NG[6] | 12.5 | NG |
| Cephalothin (7.1 ug/ml) | NG | 15.7 | NG |
| Clindamycin (7.1 ug/ml) | NG | 13.5 | 24.3 |
| Erythromycin (7.1 ug/ml) | NG | 12.3 | 12.3 |
| Gentemycin (4.0 ug/ml) | NG | 12.0 | 12.8 |
| Methicillin (3.6 ug/ml) | NG | 12.2 | 14.5 |
| Tetrocycline (7.1 ug/ml) | NG | 12.5 | 14.0 |
| Tobramycin (4.0 ug/ml) | NG | 11.7 | 13.2 |

[1]Initial innoculum was approximately 10 to 100 cfu/ul.
[2]Time to Detection was given automatically by the BacT/Alert Microbial Detection System.
[3]C = high activity charcoal bound to cellulose fibers.
[4]Triton X-100 treated high activity charcoal bound to cellulose fibers.
[5]The concentration of antibiotics used were above the minimal inhibitory concentrations of *S. aureus* ATCC 12600.
[6]NG = No Growth

We claim:

1. A device for the enhanced recovery and detection of microorganisms and for continuously monitoring biological activity in a sample comprising a sealable, sterilizable, specimen container, having an internal chamber in which a sample may be cultured, the internal chamber enclosing a sterile culture medium and an adsorbent in an amount that is effective for neutralizing, binding, or inhibiting antimicrobial substances present in said sample and said medium, the container having at least one transparent section therein and a sensor means located inside said container in the region of the transparent section, said sensor means comprising a membrane and an indicator medium, the indicator medium being selected for its ability to exhibit a detectable change when exposed to products of an organism's metabolic activity whereby changes in the appearance of the sensor means can be continuously monitored from the exterior of said container through said transparent section, thereby monitoring biological activity without violating the integrity of said container after sealing.

2. The device according to claim 1, wherein said adsorbent is selected from the group consisting of aluminum oxide, colloidal native hydrated aluminum silicates, crystalline hydrated alkali-aluminum silicates, silica, siliceous frustules, fragments of various species of diatoms, amorphous carbon, ion exchange resins, non-functional polymeric resin adsorbents, polystyrene resin cross-linked with divinyl benzene and combinations thereof.

3. The device according claim 1, wherein said adsorbent is selected from the group consisting of charcoal bound to fibers, fuller's earth bound to fibers and charcoal bound to fuller's earth.

4. The device according to claim 1, wherein said adsorbent comprises activated charcoal bound to fuller's earth.

5. The device according to claim 1, wherein said adsorbent comprises a mixture of activated charcoal bound to cellulose fibers and fullers earth bound to cellulose fibers.

6. The device according to claim 1, wherein said adsorbent comprises a resin capable of isolating antimicrobial material present in the sample.

7. A method for neutralizing antimicrobial substances in a culture medium and a sample to enhance the recovery and detection of microorganisms in said sample comprising:
   a) preparing culture medium,
   b) adding to said medium at least one non-resinous adsorbent in an amount that is effective for neutralizing, binding or inhibiting antimicrobial substances, and
   c) adding the sample to be tested to said medium containing said non-resinous adsorbent.

8. The method according to claim 7, wherein said non-resinous adsorbent is selected from the group consisting of aluminum oxide, colloidal native hydrated aluminum silicates, crystalline hydrated alkali-aluminum silicates, silica, siliceous frustules and fragments of various species of diatoms, amorphous carbon and combinations thereof.

9. The method according to claim 7, wherein said non-resinous adsorbent is selected from the group consisting of charcoal bound to fibers, fuller's earth bound to fibers and charcoal bound to fuller's earth.

10. The method according to claim 9, wherein said non-resinous adsorbent comprises activated charcoal bound to fuller's earth.

11. A method for neutralizing antimicrobial substances in a culture to enhance the recovery and detection of microorganisms in a sample comprising:
   a) providing the device of claim 1,
   b) preparing the culture medium, c) adding to said medium at least one adsorbent in amounts that are effective in neutralizing, binding or inhibiting antimicrobial substances, d) introducing the medium containing said at least one adsorbent into said device, and e) inoculating the medium with the sample.

12. A method according to claim 11, wherein said adsorbent is selected from the group consisting of aluminum oxide, colloidal native hydrated aluminum silicates, crystalline hydrated alkali-aluminum silicates, silica, siliceous frustules, fragments of various species of diatoms, amorphous carbon, ion exchange resins, non-functional polymeric resin adsorbents, polystyrene resin cross-linked with divinyl benzene and combinations thereof.

13. A method according to claim 11, wherein said adsorbent is selected from the group consisting of charcoal bound to fibers, fuller's earth bound to fibers and charcoal bound to fuller's earth.

14. A method according to claim 13, wherein said adsorbent comprises activated charcoal bound to fuller's earth.

* * * * *